(12) United States Patent
Yoon et al.

(10) Patent No.: US 7,311,440 B2
(45) Date of Patent: Dec. 25, 2007

(54) ANATOMICALLY CONFORMING INTRAORAL DENTAL RADIOGRAPHIC SENSOR

(75) Inventors: Douglas C. Yoon, Beverly Hills, CA (US); Adam Chen, Los Angeles, CA (US)

(73) Assignee: Cyber Medical Imaging, Inc., Beverly Hills, CA (US)

( * ) Notice: Subject to any disclaimer, the term of this patent is extended or adjusted under 35 U.S.C. 154(b) by 142 days.

(21) Appl. No.: 10/813,499

(22) Filed: Mar. 31, 2004

(65) Prior Publication Data

US 2005/0226389 A1    Oct. 13, 2005

(51) Int. Cl.
*H05G 1/64* (2006.01)
*A61B 6/14* (2006.01)

(52) U.S. Cl. .................... 378/207; 378/98.8; 378/163; 378/191; 250/370.09

(58) Field of Classification Search ............... 378/98.8, 378/163–165, 167–171, 189, 191, 207; 250/370.09
See application file for complete search history.

(56) References Cited

U.S. PATENT DOCUMENTS

| | | | | | |
|---|---|---|---|---|---|
| 1,286,251 | A | * | 12/1918 | Dorr | 378/170 |
| 2,240,336 | A | * | 4/1941 | Kreider | 378/168 |
| 2,553,028 | A | * | 5/1951 | Wright | 378/170 |
| 4,941,164 | A | * | 7/1990 | Schuller et al. | 378/205 |
| 4,949,370 | A | * | 8/1990 | Tanaka | 378/170 |
| 5,166,967 | A | * | 11/1992 | Fabian | 378/168 |
| 5,359,637 | A | * | 10/1994 | Webber | 378/2 |
| 5,416,822 | A | * | 5/1995 | Kunik | 378/162 |
| 5,691,539 | A | * | 11/1997 | Pfeiffer | 250/370.09 |
| 5,896,437 | A | * | 4/1999 | Ploetz | 378/2 |
| 5,970,119 | A | * | 10/1999 | Hofmann | 378/163 |
| 6,169,781 | B1 | * | 1/2001 | Doebert et al. | 378/98.8 |
| 6,196,715 | B1 | * | 3/2001 | Nambu et al. | 378/197 |
| 6,229,873 | B1 | * | 5/2001 | Bani-Hashemi et al. | 378/63 |
| 6,320,934 | B1 | * | 11/2001 | Carroll et al. | 378/98.8 |
| 6,461,038 | B2 | * | 10/2002 | Pellegrini et al. | 378/191 |
| 6,652,141 | B1 | * | 11/2003 | Cianciosi | 378/191 |
| 6,652,142 | B2 | * | 11/2003 | Launay et al. | 378/205 |
| 6,811,312 | B2 | * | 11/2004 | Bratslavsky et al. | 378/191 |
| 6,890,099 | B2 | * | 5/2005 | Tanaka et al. | 378/205 |
| 6,960,020 | B2 | * | 11/2005 | Lai | 378/207 |
| 7,140,769 | B2 | * | 11/2006 | Kay | 378/168 |
| 2004/0011976 | A1 | * | 1/2004 | Kay | 250/580 |

OTHER PUBLICATIONS

R. K. W. Schulze and B d'Hoedt, "A method to calculate angular disparities between object and receptor in paralleling technique", Dentomaxillofacial Radiology 31, 32-38 (2002).*

Ralf Schulze et al., "Determination of projection geometry from quantitative assessment of the distortion of spherical references in single-view projection radiography", Med. Phys. 31 (10), 2849-2854 (2004).*

* cited by examiner

*Primary Examiner*—Allen C. Ho
(74) *Attorney, Agent, or Firm*—Matthew F. Jodziewicz (57) ABSTRACT

A system is described for obtaining intraoral radiographic images using an anatomically conforming sensor and a method is described for correcting the projective distortions caused by the inclination of the plane of the imaging sensor relative to the x-ray beam. The purpose of the described sensor system is to reduce patient discomfort as compared to conventional planar intra-oral x-ray sensors, which tend to impinge on sensitive tissues within the oral cavity. An additional purpose of the described system is to allow for better coverage of the subject by allowing the sensor to fit closer against the surrounding tissues.

6 Claims, 5 Drawing Sheets

ANATOMICALLY CONFORMING INTRAORAL DENTAL RADIOGRAPHIC SENSOR

FIELD AND BACKGROUND OF THE INVENTION

The present invention relates to an intraoral sensor design to be applicable to radiographic imaging sensors such as film, storage phosphor devices or solid-state direct capture devices (e.g. CCD's or CMOS based devices) or any other imaging sensor that can be used to produce radiographic images. Such sensors may be components of radiographic imaging systems that may include computers and video monitors for displaying radiographs. The present invention is also directed toward a method of correcting distortions appearing in the images of such radiographic imaging systems caused by the non-perpendicularity of the x-ray source relative to the imaging surface. Such analyses may be performed on a PC, which in turn may be part of a digital radiographic imaging system. The illuminating x-ray radiation source for such sensors and radiographic imaging systems is not the subject of the present invention.

Radiographs are fundamental to most dental diagnostic procedures. However, a common complaint and problem during radiographic exams is patient discomfort during the placement of radiographic sensors within the mouth. The majority of these complaints involve the placement of the radiographic sensor in the posterior maxillary and mandibular arches of the patient. This problem is primarily due to the limited space available for proper placement of the sensors within these regions. This has been a problem since the inception of dental radiography using standard x-ray film technology.

A common method used to reduce such patient discomfort is to bend portions of the film package to conform to the anatomic shape of the mandibular or maxillary arches. However this bending contributes to the problems of image distortion of the intended subject as described below.

Recently, solid-state x-ray sensors have been developed that replace film. The patient discomfort problem for these sensors is even greater because these devices are rigid by nature and cannot be bent like film. With these rigid sensors, the only recourse is to place the sensor at a more comfortable angle and position for the patient, but such positioning is normally not optimal for a diagnostic radiograph of the intended subject. One study has shown that using such rigid devices results in more sensor placement errors than conventional film, thus requiring more retakes to produce clinically acceptable radiographs (C.H. Versteeg, et. al., *An evaluation of periapical radiology with a charge-coupled device*, Dentomaxillofacial Radiology, 1998, 27: 97-101).

Both of these approaches, using film and rigid sensors, result in a distorted radiographic image of the intended subject when the x-ray beam is not perpendicular to the imaging plane.

Thus, a need exists to provide for a more comfortable sensor configuration while correcting for the projective distortions of the images produced when the x-ray beam is not perpendicular to the imaging plane.

OBJECTS AND SUMMARY OF THE PRESENT INVENTION

Accordingly, an object of the present invention is to provide a configuration for a radiographic sensor that allows for increased patient comfort.

Another object of the present invention is to provide a configuration for a radiographic sensor that allows for improved coverage of the radiographic subject.

Yet another object of the present invention is to provide for the incorporation of fiduciary elements within a radiographic sensor that allows for the measurement of the magnitude of image distortion produced when the imaging x-ray beam is not perpendicular to the sensor surface.

Finally, another object of the present invention is to provide a method for the correction of distortions in a radiographic image that results when the x-ray beam is not perpendicular to the plane of the sensor.

The present invention is embodied in a radiation sensor that has a specific geometric shape or configuration that not only provides more comfort to a patient while in intraoral use, but one that is capable of providing a more accurate image of the area of concern by eliminating distortions of the resultant image normally found in other modern radiographic imaging systems and sensors. Such systems and sensors typically operate in conjunction with personal computer systems (PC's) whose function is to serve as a platform to receive, analyze, display and archive image data received from the sensor systems.

The preferred geometric configuration of a x-ray radiation imaging sensor that embodies the present invention is unique among known intraoral radiographic imaging sensors in that it divides the radiographic imaging sensor into several discrete sections, each section imaging a different region of the subject.

Furthermore such sections are arranged in a fashion that conforms to the anatomic curvatures of the human maxilla and mandible while maintaining a diagnostically useful image and contiguous coverage of the subject. To accomplish this the different sensor sections may be oriented in different directions, resulting in a non-planar shape.

Also, the sections of the sensor are abutted together in a fashion that yields contiguous coverage of the subject area. Finally, each section has incorporated within it radio-opaque fiduciary elements of known shape and size whose projected radiographic images indicate the orientation of the x-ray beam relative to the surface of each of the sensor sections.

Another embodiment of the present invention involves a method of processing of image data produced by the hardware that also embodies the present invention. This processing method includes steps that use the image of a fiduciary element, whose shape and size is known, to correct the projective distortions in the resultant radiographic image caused by non-perpendicularity of the x-ray beam relative to the surface of the sensor section.

Such inclination of the incident x-ray beam causes a projective distortion of the radiographic image of the fiduciary element, as well as the radiographic image of the intended subject. Because the shape and size of the fiduciary element is known, the precise orientation of the x-ray beam can be derived from the nature of the distorted image using principles of projective geometry. In turn, the resultant distorted radiographic image can be restored to its undistorted state from knowledge of the beam orientation through a reverse projective transformation of the image, again using principles of projective geometry. This method of the invention is concerned with image distortion and restoration and is independent of the number of sensor sections and applies even to sensors consisting of only one section.

In general, one embodiment of the present invention is found in a radiation sensor that is intended for use with a digital intraoral radiographic imaging system for placement in the mouth of a patient for production of radiographs of teeth and supporting structures. Such a sensor includes a housing containing at least two generally planar, radiation detectors abutting at a non-zero angle forming a generally contiguous convex or concave image capturing surface oriented toward a radiation source. The housing shape is selected to conform to the anatomical curvatures of the human maxillary and mandibular arches of the average patient. At least one radio-opaque fiduciary element of known shape, size and location is embedded on, in or just under the housing intermediate to the radiation source and to the surface of each of the radiation detectors. The fiduciary elements cast a projected image on the surfaces of the radiation detectors when illuminated by an x-ray source for use in eliminating distortions in the image captured by the sensor.

Another embodiment of a sensor containing the present invention includes a radiation sensor also intended for use with a digital intraoral radiographic imaging system for placement in the mouth of a patient for production of radiographs of teeth and supporting structures that conforms to the anatomic oral structure of the patient in a manner that provides less distortion in the detected image than that of current sensors. In this embodiment the sensor is enclosed in a housing containing at least two generally planar, radiation detectors abutting at a non-zero angle to form a faceted, generally contiguous convex or concave image capturing surface oriented toward a radiation source. The angle is selected such that the sensor housing conforms to the anatomical curvatures of the human maxillary and mandibular arches of the average patient. In this embodiment, each adjoining pair of generally planar radiation detectors are held in a fixed angular relationship to one another or flexibly joined so that the angle at which they abut can be changed to allow the housing to conform more easily to the anatomical curvatures of the human maxillary and mandibular arches of the average patient.

Additionally, the present invention is also found in a method for correcting distortions in a radiation sensor used with a digital intraoral radiographic imaging system for placement in the mouth of a patient for the production of radiographs of teeth and supporting tissues. A method embodying the present invention includes the steps of:

Providing a housing containing at least two generally planar, radiation detectors abutting at a non-zero angle to form a faceted, generally contiguous convex or concave imaging surface oriented toward a radiation source, the angle being selected such that the sensor housing conforms more easily to the anatomical curvatures of the human maxillary and mandibular arches of the average patient;

Placing at least one radio-opaque fiduciary element of known shape, size and location intermediate to the radiation source and to the surface of at least one of the radiation detectors;

Exposing the surfaces of the radiation detectors and the fiduciary element to the radiation source to project an image of the fiduciary element and of the teeth and supporting structures onto the radiation detectors;

Capturing and digitizing for analysis the sensor output representing the projected image of the fiduciary elements and the teeth and supporting structures detected by the radiation detectors;

Analyzing the digitized data representing the image of the fiduciary element to determine the magnitude of distortion of the projected fiduciary element's shape onto the surfaces of the radiation detectors, due to the non-perpendicularity of the radiation source relative to the surfaces of the radiation detectors in comparison to that of an ideal undistorted image of the fiduciary element projected onto the surfaces of the radiation detectors by exposure to a radiation source that is perpendicular to the surfaces of the radiation detectors, and determining a corrective transformation that transforms the distorted image of the projected fiduciary element into that of an undistorted image of the fiduciary elements; and, Applying the corrective transformation to the digitized image data to transform the distorted projected image of the teeth and supporting structures to that of an undistorted projected image of the teeth and supporting structures.

Various additional objects and advantages of the present invention will become apparent from the following detailed description.

DESCRIPTION OF THE PREFERRED EMBODIMENT OF THE INVENTION

Figure 1A:
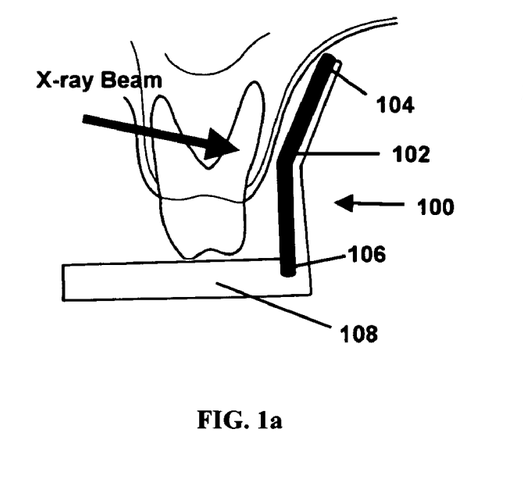
FIG. 1a is a cross-sectional view through the posterior portion of the maxilla illustrating an anatomically shaped radiographic sensor embodying the present invention.

Referring now to the Figures, a sensor embodying the present invention is shown generally at 100 in FIG. 1a. The simplest implementation of an anatomically shaped radiographic sensor 102 embodying the present invention has two abutted imaging planes 104, 106, respectively, as shown in FIG. 1a which illustrates a cross-sectional view through the posterior portion of a patient's maxillary arch. A sensor holder/positioner 108 is shown for retention between a patient's teeth to hold sensor 102 in position during imaging procedures.

The specific angle of the two imaging planes 104, 106 relative to each other is not critical but empirical testing indicates that angles of about 20-40 degrees result in significant patient comfort relative to a single flat plane of equivalent imaging area. This configuration has been shown to significantly improve comfort and improve subject coverage compared to a standard sensor.

Figure 1B:
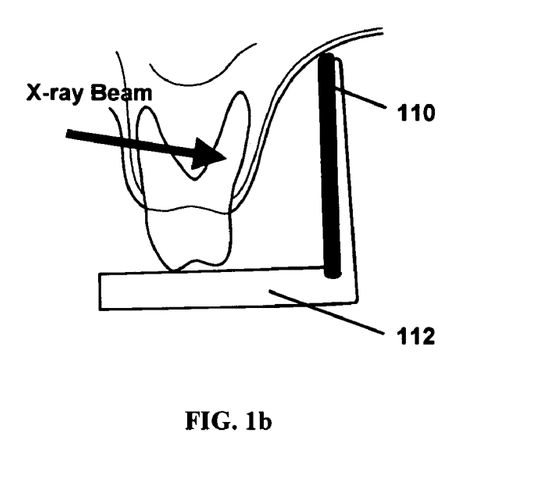
FIG. 1b is a cross-sectional view through the posterior portion of the maxilla showing the placement of a conventional radiographic sensor and illustrating the potentially painful impingement of the sensor on the soft tissues of the palate.

FIG. 1b is a similar view of a conventional radiographic sensor 110 and its corresponding sensor holder/positioner 112 illustrating the potentially painful impingement of the sensor on the soft tissue of the maxillary palate and the unfavorable imaging placement due to the increased distance of the sensor relative to the teeth and supporting structures.

Figure 2A:
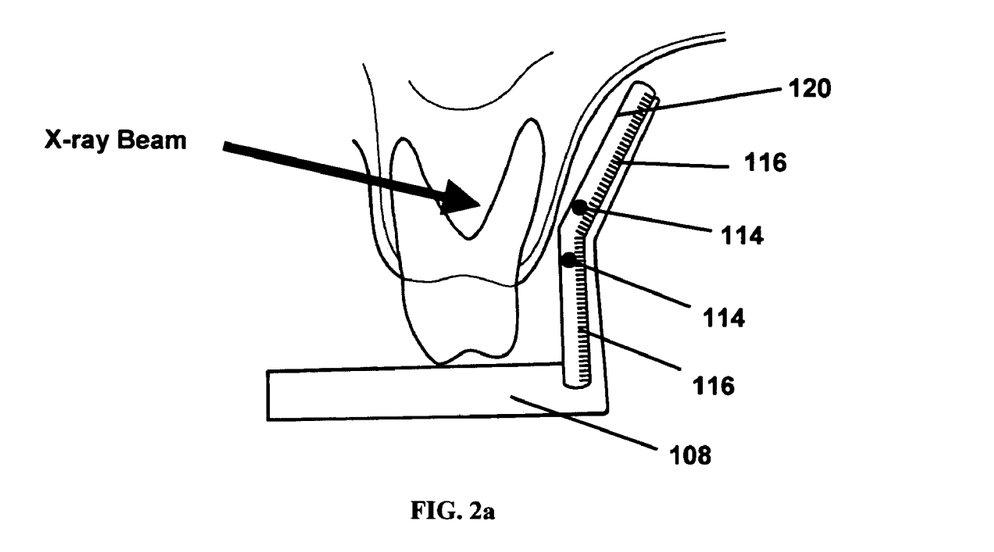
FIG. 2a is a cross-sectional view through the posterior portion of the maxilla and an internal cross-sectional view of a section of an intraoral sensor illustrating an alternate anatomically shaped radiographic sensor with housing, radiation detectors and incorporated fiduciary elements embodying the present invention.

FIG. 2a shows the placement of fiduciary elements 114 relative to the surfaces of the radiation detectors 116 of the sensor 102 and its housing 120. Criteria for such elements include: 1) a size sufficiently small to minimize obstruction of critical features in the radiograph, 2) a size large enough to allow precise length measurement of the element relative to the resolution of the sensor, 3) radio-opacity of the element and, 4) as a manufacturing consideration the fiduciary element should be symmetrical in shape so that its precise orientation on the sensor is not critical.

Figure 2B:
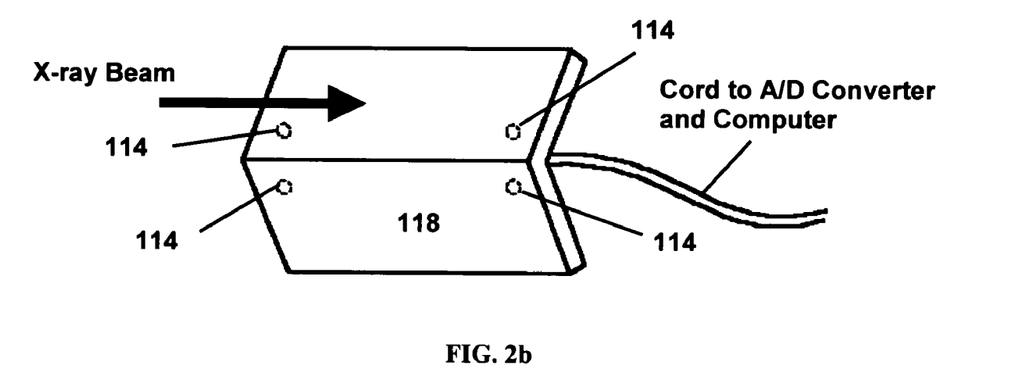
FIG. 2b is a frontal view of an alternate anatomically shaped radiographic sensor similar to that shown in FIG. 2a illustrating a possible spatial distribution of fiduciary elements within a sensor embodying the present invention.

FIG. 2b shows a frontal view of the preferred embodiment, illustrating the placement of the fiduciary elements 114 relative to the sensor surface 118. Size and placement of such fiduciary elements 114 should strive to ensure imaging of at least one element per section of sensor, despite misaiming of the illuminating x-ray beam while minimizing obscuration of the intended subject.

Thus, in the preferred embodiment a 1 mm diameter stainless steel symmetric sphere has been selected as the fiduciary element 114 being illustrated. This is because stainless steel offers sufficient radio-opacity to the imaging X-ray beam, and also because currently available high-resolution CCD sensors typically have a pixel resolution of 0.022 millimeters (22 microns). Hence, the size measurement of the element should be accurate to about two percent (more than adequate for most dental diagnostic applications). Film offers even higher measurement accuracy.

The image distortions caused by non-perpendicularity of the illuminating x-ray beam relative to the surface of the radiation detector belong to a general class of mathematical functions known as projective transforms. Moreover, if the illuminating source is relatively far from the intended subject (far field approximation), a good approximation for dental imaging, then the distortion belong to a special sub-class of projective transforms known as affine transforms. In the case of the preferred embodiment such transforms result in a skewing or tilting of the image at angle $\phi$ and stretching of the image by a factor $f$, as given by the following general equation:

$$x' = x + y \cdot f \cdot \cos(\phi)$$

and $$y' = y \cdot f \cdot \sin(\phi) \quad \text{EQ. 1}$$

where, (x, y) are the original image coordinates and (x', y') are the equivalent transformed or distorted image coordinates.

More importantly, if the values for the parameters $\phi$ and $f$ can be determined then the image distortion effects can be corrected for by applying the reverse transformation of EQ. 1 as given by:

$$x = x' - \frac{y' \cdot \cos(\phi)}{\sin(\phi)} \text{ and } y = \frac{y'}{f \cdot \sin(\phi)} \quad \text{EQ. 2}$$

where, (x, y) are the original image coordinates and (x', y') are the equivalent transformed or distorted image coordinates.

In turn, from geometric principles, the parameters $\phi$ and $f$ are determined by the orientation of the illuminating x-ray beam relative to the surface of the radiation detector. Specifically, the skew angle, $\phi$, is equal to the beam azimuthal angle and the stretch factor, $f$, in the far field depends upon the inclination angle, $\theta$, of the beam relative to a perpendicular to the surface of the radiation detector by the relationship:

$$f_\theta = \frac{1}{\cos(\theta)} \quad \text{EQ. 3}$$

However, it can be readily seen that the angle, $\phi$ and factor, $f$ in EQ. 2 can be directly obtained from the extent and direction of elongation of the image of the spherical fiduciary element captured by the sensor, which is essentially the shadow of the fiduciary element cast upon the surface of the radiation detector by the illuminating x-ray beam.

Figure 3A:
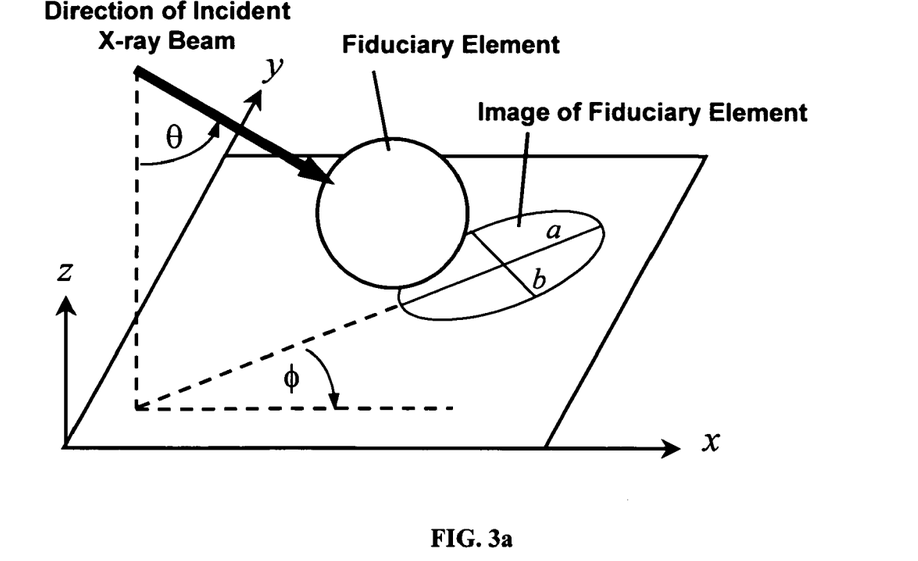
FIG. 3a is an idealized schematic showing the projective geometrical relationship of a fiduciary element onto a plane.
Figure 3B:
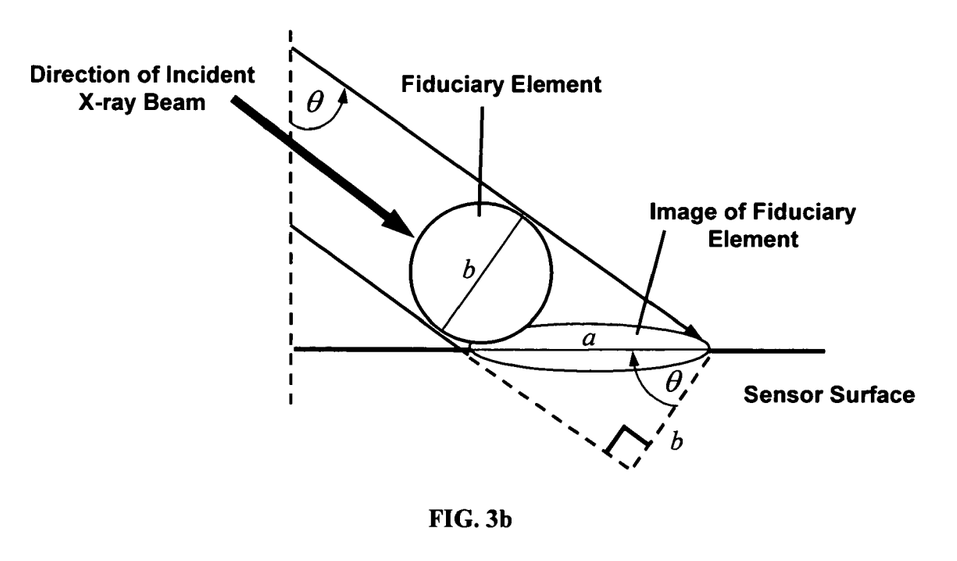
FIG. 3b is a schematic showing the internal geometric arrangement of a fiduciary element with respect to the surface of the radiation detector in a section of a sensor and its projected image thereon.

FIGS. 3a and 3b are idealized schematics illustrating the geometric arrangement of a fiduciary element 114 with respect to the surface of the radiation detector 118 and the illuminating x-ray beam and the resulting image. Note that if the direction of the x-ray beam is perpendicular to the surface of the surface of the radiation detector, the image will be a circle. FIG. 3b shows the relationship between the beam inclination angle, $\theta$, and the length of the major axis, a, under the far field assumption. The relationship defined in EQ. 3 can readily be deduced from FIG. 3b. Note that the length of the minor axis, b, is the same as the diameter of the fiduciary element.

From FIG. 3a it can be seen that if the beam is not perpendicular to the surface of the radiation detector then the shadow will be elongated and slanted or skewed at the same angle as the beam azimuthal angle, $\phi$. Also, under the far field assumption, the shape will be an ellipse, where the length of the minor axis, b, will be the same as the diameter of the fiduciary element and the length of the major axis, a, will be longer than b by the factor, $f$, hence:

$$f = \frac{a}{b} \quad \text{EQ. 4}$$

Even in the case of a non-planar parallel x-ray beam, more specifically, a divergent beam, the above derivation for $f$ is robust. The beam divergence, here designated by $\Delta\theta$, for most intraoral dental applications is typically less than 5 degrees. The error for $f$, defined as $f_{(\theta+\Delta\theta)} - f_\theta$ and denoted as $\Delta$, can be calculated in terms of the beam divergence. More specifically, it can be shown from EQ. 3 that the fractional error for $f$, defined as $\Delta f/f$, is approximately:

$$\frac{\cos(\theta)}{\cos(\theta + \Delta\theta)} - 1 \qquad \text{EQ. 5}$$

For θ=0 degrees and Δθ=5 degrees the fractional error is less than 0.004 or 0.4 percent. For values of θ as large as 30 degrees and Δθ=5 degrees the fractional error is less then 0.06 or 6 percent.

In addition, the error in the estimate of the skew or azimuth angle, φ, is not affected by beam divergence.

In practice, the parameters a, b and φ, for the elliptical images of the fiduciary elements ellipse can be extracted from the image data using image processing techniques and numerical methods. In the preferred embodiment this analysis is performed on a digital representation of the radiograph. Note that the actual image-capture technology for a digitized radiograph is not the subject of the present invention. Such images may be obtained indirectly by scanning conventional film radiographs with currently available digital film scanners or obtained directly using existing digital radiographic image capture technology such as storage phosphor plates or CCD/scintillator or CMOS/scintillator combinations.

Figure 4:
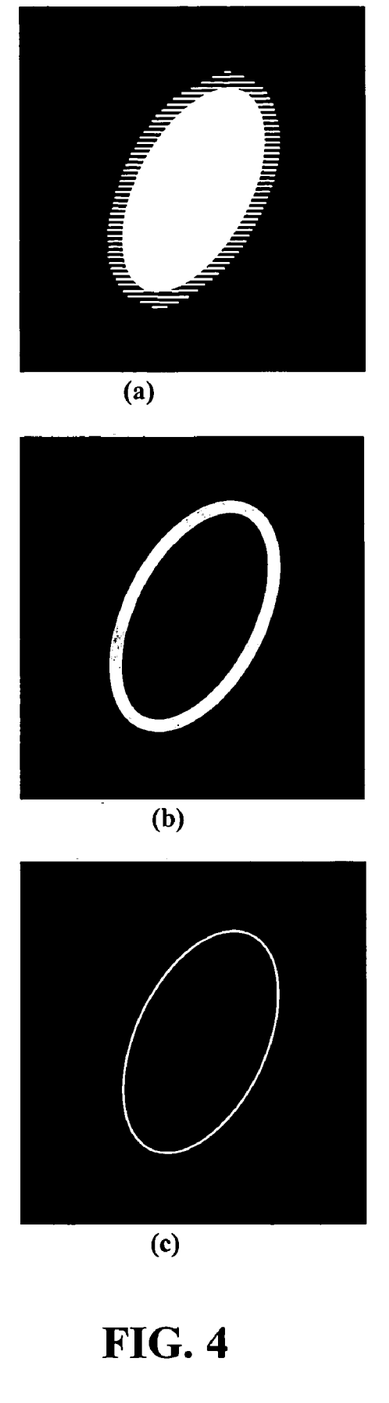
FIG. 4a is an image of a spherical fiduciary element projected onto a sensor's radiation detector's surface.
FIG. 4b is an image of the spherical fiduciary element projected onto a sensor's radiation detector's surface as in FIG. 4a after the application of an edge filtering transformation to the image data.
FIG. 4c is the image of FIG. 4a after the image has been subjected to threshold and thinning filters.

The processing of image data in the preferred embodiment of the present invention is accomplished in two steps. First, the region of the digitized radiographic image that includes a fiduciary element is isolated based on its known position on the sensor. An example of such an image is shown in FIG. 4a for a spherical fiduciary element. Note the elliptical shape of the image due to the non-perpendicularity of the x-ray beam relative to the surface of the radiation detector capturing the image.

Next, the edges of the ellipse are emphasized using gradient filtering (e.g. Sobel filter) as illustrated in FIG. 4b. An intensity threshold is applied to the filtered image to extract image points in the edge region of the ellipse, and then these points are thinned or eroded using standard numerical techniques in order to more precisely define the edge region. These extracted points are shown in FIG. 4c. These points are used in the derivation of the curve fitting parameters. To this end, the set of extracted edge points (white points) in FIG. 4c are tabulated in terms of their pixel coordinates (i.e. x and y pixel coordinates).

The coordinates of the tabulated points are applied to the fitting of an equation for a generalized ellipse oriented at angle, φ, with major axis length, a, and minor axis length, b, and centered about ($x_0$, $y_0$) as given by:

$$\frac{\left[\frac{(x-x_0)\cdot\cos(\phi)-}{(y-y_0)\cdot\sin(\phi)}\right]^2}{a^2} + \frac{\left[\frac{(x-x_0)\cdot\sin(\phi)+}{(y-y_0)\cdot\cos(\phi)}\right]^2}{b^2} = 1 \qquad \text{EQ. 6}$$

Note that EQ. 6 is not the same as the image distortion transformation due to beam non-perpendicularity, but rather just the equation of a rotated ellipse used to estimate the orientation parameters of interest, φ, a, b.

The best estimate for the unknown parameters, φ, a, b, $x_0$, and $y_0$ are derived through least squares error minimization, minimizing the summed squared error between the coordinates of the tabulated extracted feature points and their corresponding equivalent points on the parameterized ellipse given by EQ. 6. In the preferred embodiment, an initial estimate is made for the unknown parameters based on an undistorted image and corresponding pairs of points are found by taking the nearest point on the parameterized ellipse to each extracted feature point. This approach, when applied iteratively, rapidly converges to an error minimum. In general, all such methods of initial parameter approximation and method of pairing corresponding points is claimed.

Once the best estimate for the unknown parameters, φ, a, b, $x_0$, and $y_0$ are derived one can then use the estimate of the parameters a and b to calculate the factor f through EQ. 4

Note that in this specific example, the expression is not linear in all the parameters, φ, a, b, $x_0$, and $y_0$, thus linear least squares fitting methods do not apply. However, numerous non-linear methods exist, such as iterative application of gradient descent error minimization. Also note, the use of other shapes for fiduciary elements, in other embodiments of the present invention may be chosen that offer more direct solutions to the orientation parameters. Finally, other methods besides least squares error minimization may be applied to derive estimates of the beam orientation parameters. The present invention is intended to cover all such fiduciary element configurations and methods of deriving orientation parameters from the image of such elements.

The final step is to apply the corrective transformation in EQ. 2 to the digitized image based on the derived values φ and f.

Figure 5A:
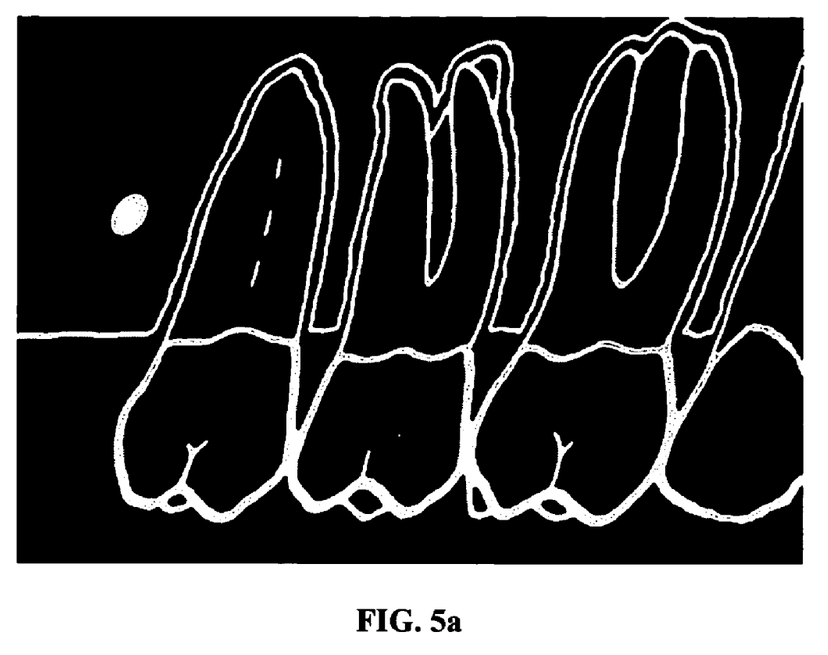
FIG. 5a illustrates a distorted image of maxillary teeth due to excessive x-ray beam inclination; and, FIG. 5b illustrates a corrected image of the distorted image of maxillary teeth as shown in FIG. 5a using the distortion of the projected images of the spherical fiduciary elements as a guide in correcting the distortion in the projected image plane.

As an example of the effectiveness of the technique, FIG. 5a shows an example of a radiographic image from a bi-planar sensor with imbedded 1 mm spherical fiduciary elements. Note the distortion, specifically elongation, of the roots of each maxillary tooth and the corresponding elongation of the fiduciary elements due to excessive x-ray beam inclination.

Figure 5B:
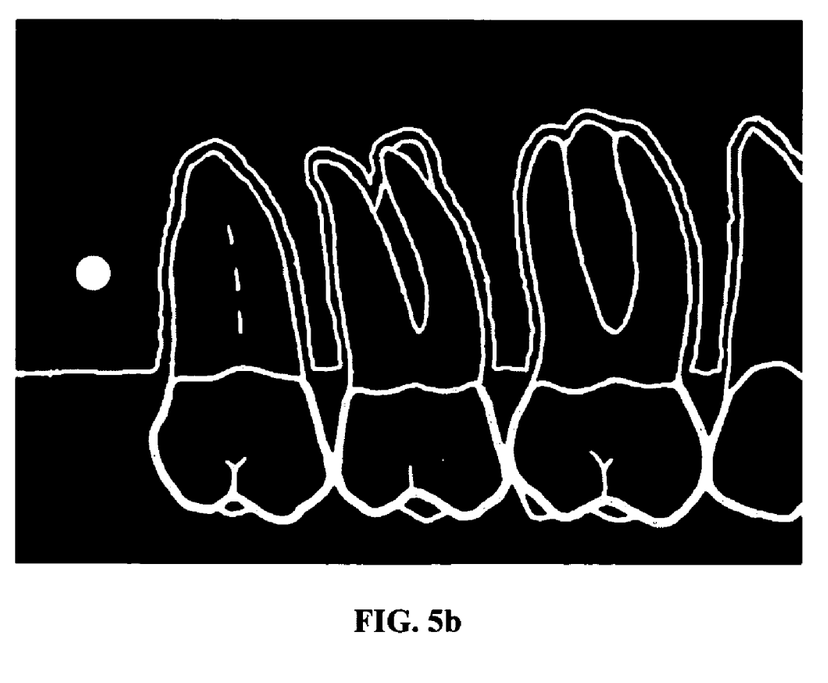

FIG. 5b shows the result of correction of the image in FIG. 5a using the extent of elongation of the fiduciary elements to correct the image. Note with the corrected image the fiduciary elements are restored to a circular shape.

In view of the above, it will be seen that the several objects of the invention are achieved and other advantageous results attained.

As various changes could be made in the above construction and methods without departing from the scope of the invention, it is intended that all matter contained in the above description or shown in the accompanying drawings shall be interpreted as illustrative and not in a limiting sense.

We claim:

1. A digital radiation sensor for intraoral placement in a mouth of a patient for production of radiographs of teeth and their anatomical supporting structures of bone, periodontal ligaments and gingiva around the root and cervical region of the tooth, said sensor comprising:

a housing containing at least one generally planar, radiation detector providing a digital imaging surface oriented toward a radiation source, said housing conforming to the anatomic curvatures of the human maxillary and mandibular arches of an average patient; and, at least one radio-opaque fiduciary element of known shape, size and location, in a known, permanently fixed spatial position to said digital imaging surface, having a known projected image shape produced by a known angle of incidence between the radiation source and said imaging surface intermediate the radiation source and the surface of said at least one radiation detector, said at least one fiduciary element casting a projected image on said at least one radiation detector when illuminated by a radiation source for determining an unknown angle of incidence between the radiation source and said imaging surface by comparing the projected image shape of the fiduciary element against the projected image shape of the fiduciary element generated by a known angle of incidence to correct for projective distortion in the projected image shape caused by the unknown angle of incidence, said at least one digital radiation detector comprising said at least one radio-opaque fiduciary element of known shape, size and location embedded on, in or under said housing intermediate the radiation source and the surface of each of said at least one radiation detectors, said at least one fiduciary element casting a projected image on said at least one radiation detectors when illuminated by the radiation source, said at least one digital radiation detector further providing a digitized data output representing the projected image of said fiduciary element, teeth and their anatomical supporting structures of bone, periodontal ligaments and gingiva around the root and cervical region of the tooth made on said digital imaging surface of said at least one radiation detector produced by the radiation detector for use in a digital radiography imaging system that uses the projected distorted image shape of said fiduciary element onto said digital imaging surface of said radiation detector for comparison against a known non-distorted projected image shape of said fiduciary element in order to generate a corrective transformation for correcting projected distortions in the data representing the projected images on said digital imaging surface of said sensor.

2. A digital radiation sensor as in claim 1 wherein said housing contains at least two, generally planar, radiation detectors abutting at a non-zero angle to form a faceted, generally contiguous imaging surface oriented toward the radiation source, said angle selected to conform said housing to the anatomic curvatures of the human maxillary and mandibular arches of the average patient.

3. A digital radiation sensor as in claim 2 wherein each adjoining pair of said generally planar detectors abut one another at a fixed angle.

4. A digital radiation sensor as in claim 2 wherein said fiduciary element is a sphere.

5. A digital radiation sensor as in claim 1 wherein said housing further having a holding tab protruding therefrom for retention between the teeth for holding the radiation detectors in a fixed position in the patient's mouth.

6. A method for correcting distortions in a radiation sensor used with a digital radiography imaging system for intraoral placement in a mouth of a patient for production of radiographs of teeth and their anatomical supporting structures of bone, periodontal ligaments and gingiva around the roots and cervical region of the teeth, said method comprising the steps of:

Providing a housing containing at least one generally planar, radiation detector providing an imaging surface oriented toward a radiation source, said housing conforming to the anatomic curvatures of the human maxillary and mandibular arches of an average patient;

Placing, by embedding on, or placing in or under said housing, at least one radio-opaque fiduciary element of known shape, size and location, in a permanently fixed spatial position to the detector imaging surface, intermediate a radiation source and the surface of said at least one radiation detector and placed in a fixed, known spatial orientation to the detector imaging plane, said at least one fiduciary element casting a projected image on said at least one radiation detector when illuminated by the radiation source;

Exposing said at least one radiation detector and said at least one fiduciary element to the radiation source to project an image of said at least one fiduciary element and said teeth and supporting structures onto the surface of said at least one radiation detector;

Capturing and digitizing the data representing the projected image of the fiduciary element, teeth and their anatomical supporting structures images of bone, periodontal ligaments and gingiva around the roots and cervical region of the teeth on the surface of said at least one radiation detector produced by the radiation detector;

Analyzing the digitized image data to determine the distortion of the projected fiduciary image onto the surface of the at least one radiation detectors due to the non-perpendicularity of the radiation source with respect to the surface of the at least one radiation detectors from that of an ideal fiduciary image projected onto the surfaces of the at least one radiation detectors defined by exposure of the fiduciary element to a radiation source perpendicular to the surface of the at least one radiation detectors, and determining a corrective transformation that transforms the distorted projected fiduciary image to that of the ideal fiduciary image; and, Applying the corrective transformation to the remaining digitized image data in order to transform the distorted projected image of the teeth and their anatomical supporting structures of bone, periodontal ligaments and gingiva around the root and cervical region of the tooth to that of an ideal projected image of the teeth and their anatomical supporting structures of bone, periodontal ligaments and gingiva around the roots and cervical region of the teeth.

* * * * *